US00PP20950P2

(12) United States Plant Patent
Ranney

(10) Patent No.: US PP20,950 P2
(45) Date of Patent: Apr. 27, 2010

(54) FLOWERING QUINCE PLANT NAMED 'ORANGE STORM'

(50) Latin Name: *Chaenomeles speciosa*
Varietal Denomination: Orange Storm

(75) Inventor: Thomas G. Ranney, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 12/381,213

(22) Filed: Mar. 9, 2009

(51) Int. Cl.
*A01H 5/00* (2006.01)

(52) U.S. Cl. ..... Plt./226

(58) Field of Classification Search ..... Plt./226
See application file for complete search history.

*Primary Examiner*—Annette H Para
(74) *Attorney, Agent, or Firm*—Jondle & Associates, P.C.

(57) ABSTRACT

'Orange Storm' is a new quince plant particularly distinguished by a medium-sized, upright, multi-stemmed, fruitless shrub, large, double-flowers with orange petals, and thornless stems, is disclosed.

2 Drawing Sheets

Genus and species: *Chaenomeles speciosa.*

Variety denomination: 'Orange Storm'.

BACKGROUND OF THE INVENTION

The present invention comprises a new and distinct cultivar of flowering quince, botanically known as *Chaenomeles speciosa*, and hereinafter referred to by the cultivar name 'Orange Storm'. This new flowering quince was developed through a breeding program at North Carolina State University, Mills River, N.C. 'Orange Storm' is an $F_1$ hybrid between the female parent, *Chaenomeles speciosa* 'Spitfire' (unpatented) and the male parent, *Chaenomeles speciosa* 'Dragons Blood' (unpatented). The first asexual propagation of 'Orange Storm' was carried out in June 2003 by rooting stem cuttings at the North Carolina State University, Mountain Horticultural Crops Research Station, Mills River, N.C. and has been asexually reproduced repeatedly by vegetative cuttings in North Carolina over a five year period.

'Orange Storm' roots readily from softwood cuttings treated with a basal dip of 5,000 ppm indole butyric acid (potassium salt) in water. 'Orange Storm' has been found to retain its distinctive characteristics through successive asexual propagations.

Plant Breeder's Rights for this cultivar have not been applied for. 'Orange Storm' has not been made publicly available more than one year prior to the filing date of this application.

SUMMARY OF THE INVENTION

The following are the most outstanding and distinguishing characteristics of this new cultivar when grown under normal horticultural practices at North Carolina State University, Mountain Horticultural Crops Research Station, Mills River, N.C.

1. A medium-sized, upright, multi-stemmed, fruitless shrub;
2. Large, double-flowers with orange petals; and
3. Thornless stems.

DESCRIPTION OF THE PHOTOGRAPHS

This new quince plant is illustrated by the accompanying photographs which show the plant's form, foliage and inflorescences. The colors shown are as true as can be reasonably obtained by conventional photographic procedures. The photographs were taken on Apr. 10, 2008 on 7-year-old plants, growing under field conditions in Mills River, N.C.

DESCRIPTION OF THE NEW CULTIVAR

Figure 1:
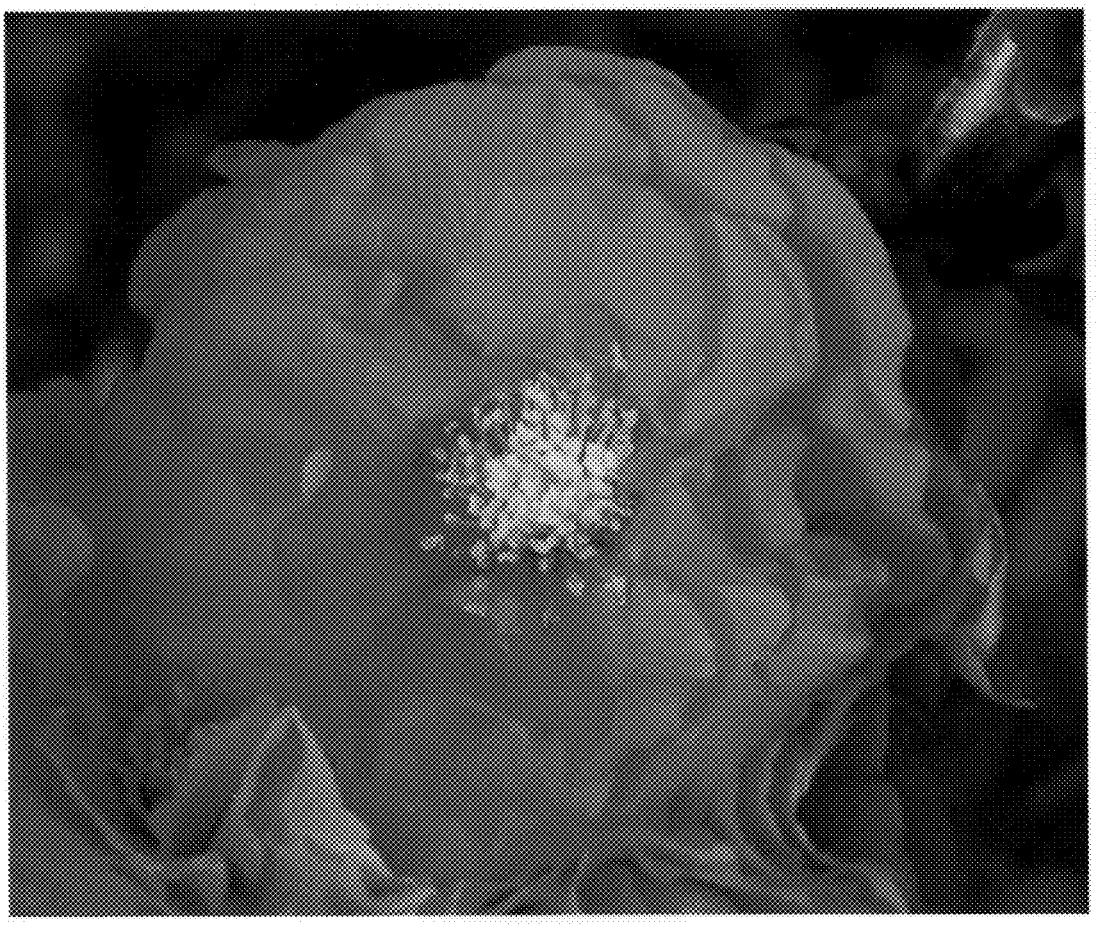
FIG. 1 shows the large, orange, double flower, prior to anthesis.
Figure 2:
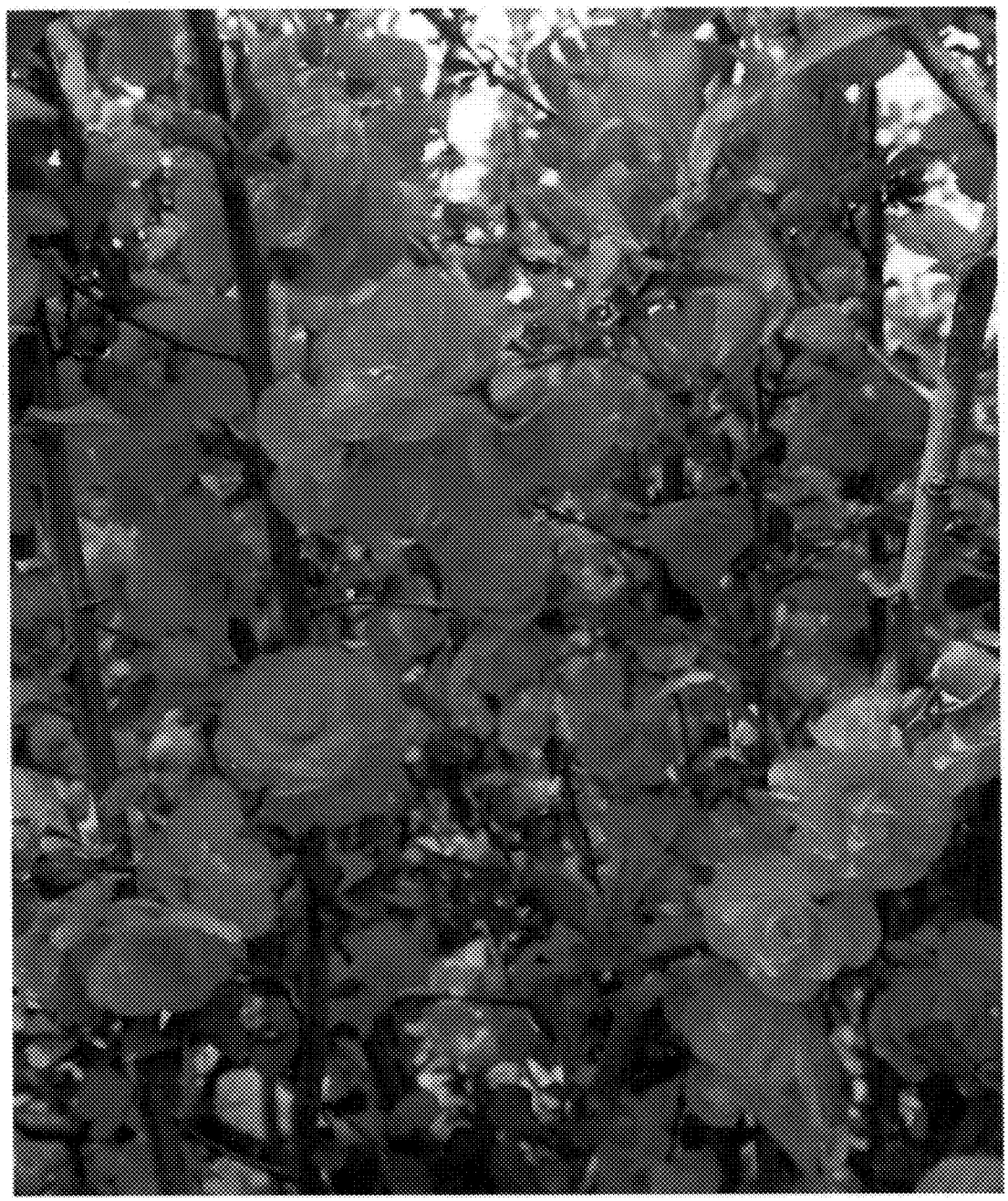
FIG. 2 shows the mature plant in full bloom.

The following detailed description sets forth the distinctive characteristics of 'Orange Storm'. The detailed description was taken on 7-year-old plants growing under landscape conditions in Mills River, N.C. in April 2008. Color references are to The R.H.S. Colour Chart of The Royal Horticultural Society of London (R.H.S.), 2001 Edition.

DETAILED BOTANICAL DESCRIPTION

Classification:
- *Botanical name.*—*Chaenomeles speciosa.*
- *Common name.*—Quince.

Parentage:
- *Female parent.*—*Chaenomeles speciosa* 'Spitfire' (unpatented).
- *Male parent.*—*Chaenomeles speciosa* 'Dragons Blood' (unpatented).

Plant description:
- *Growth habit.*—Upright.
- *Plant shape.*—Vase-shaped.
- *Height at maturity.*—2 meters to 3.33 meters.
- *Width at maturity.*—2 meters to 3.33 meters.

Stem:
- *Mature stem color.*—RHS N199B (Grey-brown).
- *Immature stem color.*—RHS 152A (Yellow-green).
- *Quantity of thorns.*—Thorns are absent.

Leaves:
- *Type.*—Deciduous.
- *Arrangement.*—Alternate.
- *Shape.*—Elliptic.

*Apex.*—Acute.
*Base.*—Attenuate.
*Margin.*—Serrulate.
*Mature leaf size.*—Length: Average is 6.10 cm (range is 5.1 cm to 7.15 cm). Width: Average is 3.65 cm (range is 3.0 cm to 4.3 cm).
*Immature leaf color.*—Adaxial (upper) surface: Flushes RHS 45B (Red), which changes to RHS 144A (Yellow-green) with some RHS 45B (Red) tinting that eventually changes to RHS 147A (Yellow-green). Abaxial (lower) surface: RHS 45B (Red) which changes to RHS 146C (Yellow-green).
*Mature leaf color.*—Adaxial (upper) surface: RHS 137A to RHS 139A (Green). Abaxial (lower) surface: RHS 147B to RHS 148B (Yellow-green).
*Stipule.*—Color: Adaxial (upper) surface: RHS 137A to RHS 139A (Green). Abaxial (lower) surface: RHS 147B to RHS 148B (Yellow-green). Size: Immature: Length: Average is 0.6 cm (range is 0.34 cm to 0.85 cm). Width: Average is 0.66 cm (range is 0.58 cm to 0.74 cm). Mature: Length: Average is 1.38 cm (range is 1.32 cm to 1.43 cm). Width: Average is 2.24 cm (range is 2.14 cm to 2.35 cm).
*Leaf attachment.*—Petiolate.
*Petiole.*—Shape: Laterally compressed. Length: Average is 0.58 cm (range is 0.56 cm to 0.6 cm). Width: Average is 0.125 cm (range is 0.1 cm to 0.15 cm). Surface: Glabrous (not pubescent).

Flower:
*Number of flowers per cluster.*—3 to 4.
*Type.*—Double flower.
*Habit.*—Seasonal (spring).
*Flowering season.*—Early spring through late spring.
*Lastingness of flower on the plant.*—7 to 21 days.
*Fragrance.*—Absent.
*Length at anthesis.*—Average is 5.4 cm (range is 4.5 cm to 6.4 cm).
*Self cleaning or persistent.*—Self cleaning.
*Petal.*—Number of petals per flower: Average is 39 (range is 31 to 49) Color, adaxial (upper) surface at anthesis: RHS 39A to RHS 42C (Orange-red). Color, abaxial (lower) surfaces at anthesis: RHS 39B to RHS 44A (Orange-red). Basal color at anthesis: RHS 35C to RHS 39D (Orange-red). Surface texture and appearance: Glabrous (not pubescent), soft, thin and lustrous (slightly shiny). Shape: Flabellate. Apex: Truncate. Base: Cuneate. Margin: Irregularly crenate. Length: Average is 2.46 cm (range is 1.55 cm to 2.9 cm). Width: Average is 1.90 cm (range is 0.73 cm to 2.5 cm). Petals, fused or unfused: Unfused.
*Peduncle.*—Shape: Cylindrical Length: Average is 0.68 cm (range is 0.55 cm to 0.80 cm). Width: Average is 0.10 cm (range is 0.05 cm to 0.15 cm). Color: Closest to RHS 144A (Yellow-green). Surface texture: Glabrous (not pubescent).

Calyx/receptacle:
*Shape and arrangement.*—5-lobed and globular to globular conical.
*Calyx/receptacle size.*—Length: Average is 1.40 cm (range is 1.23 cm to 1.54 cm). Width: Average is 1.52 cm (range is 1.38 cm to 1.68 cm). Depth: Average is 0.47 cm (range is 0.41 cm to 0.61 cm).
*Lobe number.*—5.
*Lobe apex.*—Truncate.
*Lobe base.*—Fused.
*Lobe margin.*—Ciliate.
*Lobe length.*—Average is 0.36 cm (range is 0.32 cm to 0.4 cm).
*Lobe width.*—Average is 0.70 cm (range is 0.4 cm to 1.0 cm).
*Lobe color, adaxial (upper) surfaces.*—RHS 143A (Green) and maturing to RHS 60A (Red-purple) with RHS 42A (Red) margins.
*Lobe color, abaxial (lower) surfaces.*—RHS 137D (Green).
*Lobe surface texture, adaxial (upper) surface.*—Glabrous (not pubescent).
*Lobe surface texture, abaxial (lower) surface.*—Pubescent.

Reproductive organs:
*Stamen.*—Quantity per flower: Average is 112 (range is 45 to 176). Shape: Filament. Color: Translucent RHS 142D (Green). Attachment: Dorsifixed. Length: Average is 0.6 cm (range is 0.6 cm to 1.2 cm). Width: Less than 0.05 cm. Anther: Length: Average is 0.18 cm (range is 0.1 cm to 0.275 cm). Width: Average is 0.125 cm (range is 0.1 cm to 0.15 cm). Shape: Ovoid. Color: Mostly RHS 10C (Yellow) but ranging from RHS 8C (Light-yellow) to RHS 13C (Darker-yellow). Pollen color: RHS 12C (Yellow). Pollen amount: Very sparse.
*Pistil.*—Absent.
*Ovary.*—Absent.

Fruit/seed set: No fruit or seed set has been observed.
Disease and insect resistance: No significant disease or insect pests have been observed.

COMPARISON WITH PARENTAL LINES AND KNOWN CULTIVARS

'Orange Storm' is distinguished from the female parent, *Chaenomeles speciosa* 'Spitfire' (unpatented) in that 'Orange Storm' has orange flowers, while 'Spitfire' has red flowers.

'Orange Storm' is distinguished from the male parent *Chaenomeles speciosa* 'Dragons Blood' (unpatented) in that 'Orange Storm' has orange flowers, while 'Dragons Blood' has red flowers.

Table 1 shows the differences between 'Orange Storm' and commercial varieties 'Jet Trail' (unpatented) and 'Toyo-Nishiki' (unpatented).

TABLE 1

COMPARISON TO COMMERCIAL CULTIVARS

| | Cultivar | | |
|---|---|---|---|
| Trait | 'Orange Storm' | 'Jet Trail' | 'Toyo-Nishiki' |
| Flower color | Orange, RHS 39A to RHS 44D | White, RHS N155 | Emerges White, RHS N155; Fading to Pink, RHS 49A to RHS 51C |
| Petal number per flower | 31 to 49 | 5 to 6 | 5 |
| Flower diameter | 4.5 cm to 6.5 cm | 5.0 cm to 6.0 cm | 3.0 cm to 5.6 cm |
| Pistil | Lacking | Present | Generally Present |
| Fruit | Lacking | Present | Present |
| Thorns | Lacking | Lacking | Present |

I claim:

1. A new and distinct cultivar of quince plant as shown and described herein.

* * * * *